United States Patent
Gross et al.

[11] Patent Number: 5,928,283
[45] Date of Patent: Jul. 27, 1999

[54] TELESCOPIC DEVICE FOR AN INTRAOCULAR LENS

[75] Inventors: Yosef Gross, Moshav Mazor; Isaac Lipshitz, Herzelia Pituach; Dotan Gedeon, Yehud, all of Israel

[73] Assignee: Visioncare Ltd, Yehud, Israel

[21] Appl. No.: 08/882,972

[22] Filed: Jun. 26, 1997

[51] Int. Cl.⁶ ................................................ A61F 2/16
[52] U.S. Cl. ........................................................ 623/6
[58] Field of Search ........................................... 623/6

[56] References Cited

U.S. PATENT DOCUMENTS

| | | | |
|---|---|---|---|
| 4,074,368 | 2/1978 | Levy, Jr. et al. | 623/6 |
| 4,172,297 | 10/1979 | Schlegel | 623/6 |
| 4,648,878 | 3/1987 | Kelman | 623/6 |
| 4,666,446 | 5/1987 | Koziol et al. | 623/6 |
| 4,759,761 | 7/1988 | Portroy | 623/6 |
| 4,863,468 | 9/1989 | Feinbloom et al. | 623/6 |
| 4,892,543 | 1/1990 | Turley | 623/6 |
| 5,201,762 | 4/1993 | Hauber | 623/6 |
| 5,275,623 | 1/1994 | Sarfarazi | 623/6 |
| 5,354,335 | 10/1994 | Lipshitz et al. | 623/6 |
| 5,391,202 | 2/1995 | Lipshitz et al. | 623/6 |
| 5,683,457 | 11/1997 | Gupta et al. | 623/6 |

FOREIGN PATENT DOCUMENTS

| | | |
|---|---|---|
| 212616 | 3/1987 | European Pat. Off. . |
| 97/10527 | 3/1997 | WIPO ................... 623/6 |

*Primary Examiner*—David H. Willse
*Attorney, Agent, or Firm*—Darby & Darby

[57] ABSTRACT

An intraocular lens implant for implantation in the interior of a human eye comprising a telescope body having an anterior end and a posterior end and including at least one window sealed to the telescope body at at least one of the anterior end and the posterior end and at least two lenses disposed within the telescope body intermediate the anterior end and the posterior end.

14 Claims, 4 Drawing Sheets

TELESCOPIC DEVICE FOR AN INTRAOCULAR LENS

FIELD OF THE INVENTION

The present invention relates to intraocular lens implants generally.

BACKGROUND OF THE INVENTION

Various types of intraocular lens implants are known in the patent literature. Particular reference is made to U.S. Pat. Nos. 5,391,202 and 5,354,335 of the present applicant/assignee and to the references cited therein. Other relevant references include European Published Patent Application EP-A-212616, U.S. Pat. Nos. 4,074,368; 4,172,297; 4,759,761 and 5,275,623 and French Published Patent Application 2,666,735.

The utility of intraocular lens implants is described in the above patent references. The disclosures of the above-mentioned publications are hereby incorporated by reference.

SUMMARY OF THE INVENTION

The present invention seeks to provide improved intraocular lens implants.

There is thus provided in accordance with a preferred embodiment of the present invention an intraocular implant for implantation in the interior of a human eye comprising a telescope body having an anterior end and a posterior end and including at least one window sealed to the telescope body at at least one of the anterior end and said posterior end and at least two lenses disposed within the telescope body intermediate the anterior end and said posterior end.

In accordance with a preferred embodiment of the present invention, the lenses are doublet lenses.

Preferably, the windows are generally without optical power.

In accordance with a preferred embodiment of the present invention air gaps are defined between the lenses and between the lenses and the windows.

In accordance with a preferred embodiment of the invention, one of the windows may define a prism.

In accordance with an alternative embodiment of the present invention, the lenses may be joined together by a cylindrical member disposed within the telescope body.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figure 1:
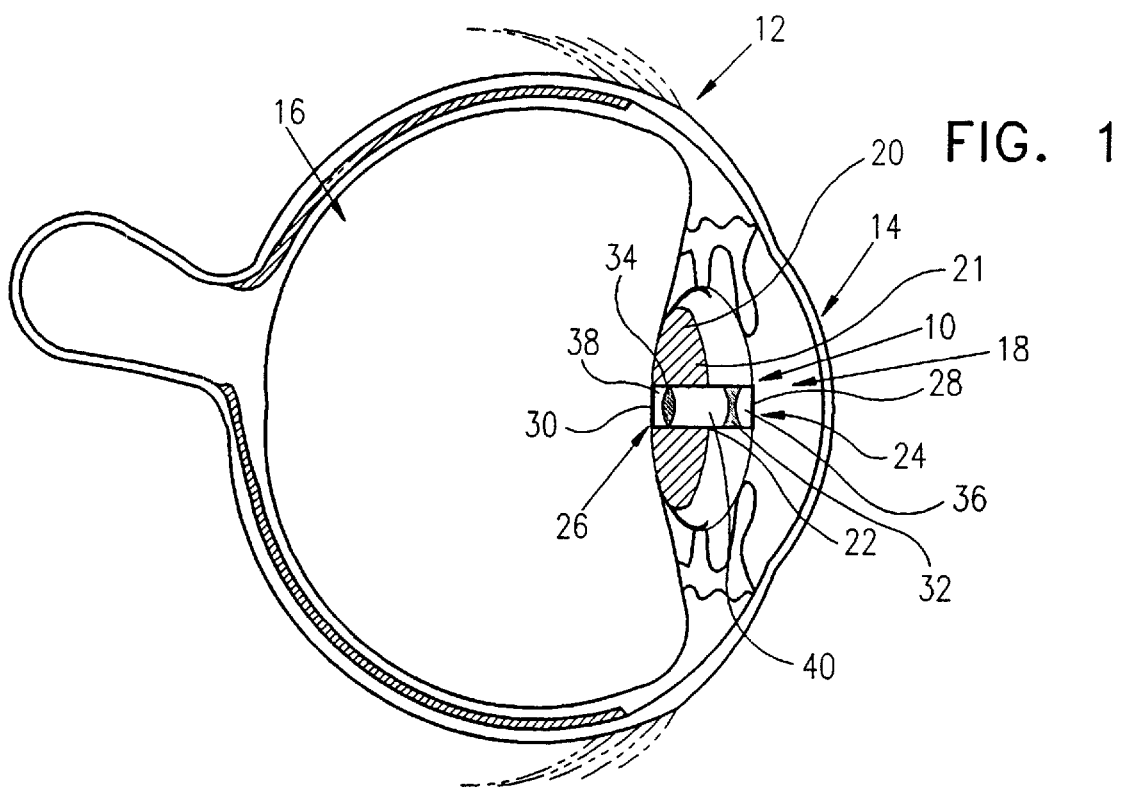
FIG. 1 is a simplified pictorial illustration of an intraocular insert constructed and operative in accordance with a preferred embodiment of the present invention located within a human eye.

Reference is now made to FIG. 1, which is a simplified pictorial illustration of an intraocular insert constructed and operative in accordance with a preferred embodiment of the present invention located within a human eye.

As seen in FIG. 1, there is provided an intraocular lens implant, indicated generally by reference numeral 10, which is implanted in the interior of a human eye 12. In the illustrated embodiment, the implant comprises a telescope 18 which preferably extends through at least a portion of a lens capsule 20 of the eye 12. The telescope 18 may extend forwardly of the lens capsule 20 toward the anterior side 14 of the eye. Alternatively it may extend posteriorly of the lens capsule or both.

In accordance with a preferred embodiment of the present invention, the telescope 18 is mounted on a carrying lens 21. Alternatively, the telescope 18 may be mounted in the lens capsule by loops or any other suitable apparatus.

In the illustrated embodiment of FIG. 1, it is seen that the telescope comprises a telescope body 22, typically of circular cylindrical configuration and formed of glass or other suitable non-porous bio-compatible material or other material which is coated with a suitable non-porous bio-compatible material.

Sealed to anterior and posterior ends 24 and 26 of the telescope body 22 are respective windows 28 and 30 which preferably do not have optical power. Mounted onto telescope body 22 intermediate windows 28 and 30 there are provided forward and rearward lenses, 32 and 34. Preferably air gaps 36 and 38 are defined between lenses 32 and 34 and respective windows 28 and 30 and an air gap 40 is defined between lenses 32 and 34.

Figure 2:
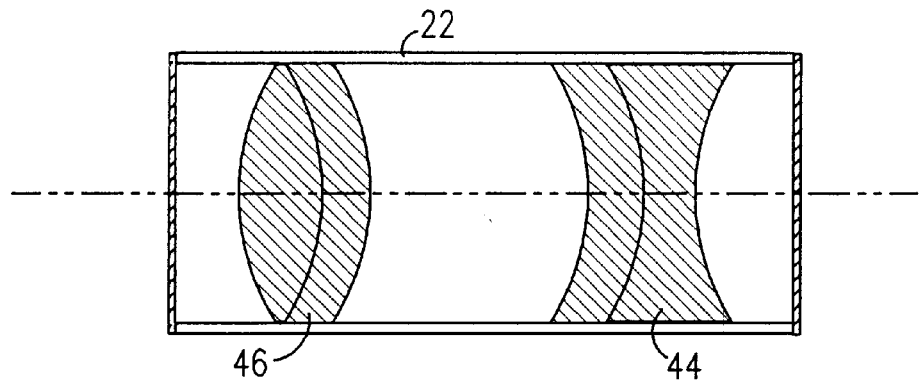
FIG. 2 is a simplified pictorial illustration of an intraocular insert of the general type shown in FIG. 1, but including joined doublet lenses.

According to an alternative embodiment of the present invention, illustrated in FIG. 2, joined doublet lenses 44 and 46 may be employed to avoid chromatic aberrations.

Figure 3:
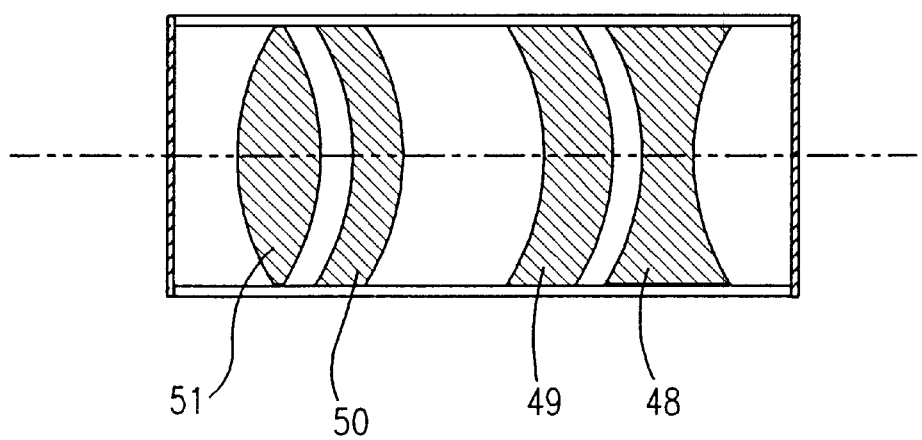
FIG. 3 is a simplified pictorial illustration of an intraocular insert of the general type shown in FIG. 2, but including separated doublet lenses.

According to a further alternative embodiment of the present invention, illustrated in FIG. 3, joined doublet lenses 48 and 49 and 50 and 51 may be employed. The configuration of FIG. 3 may be used to provide enhanced optical power.

Figure 4:
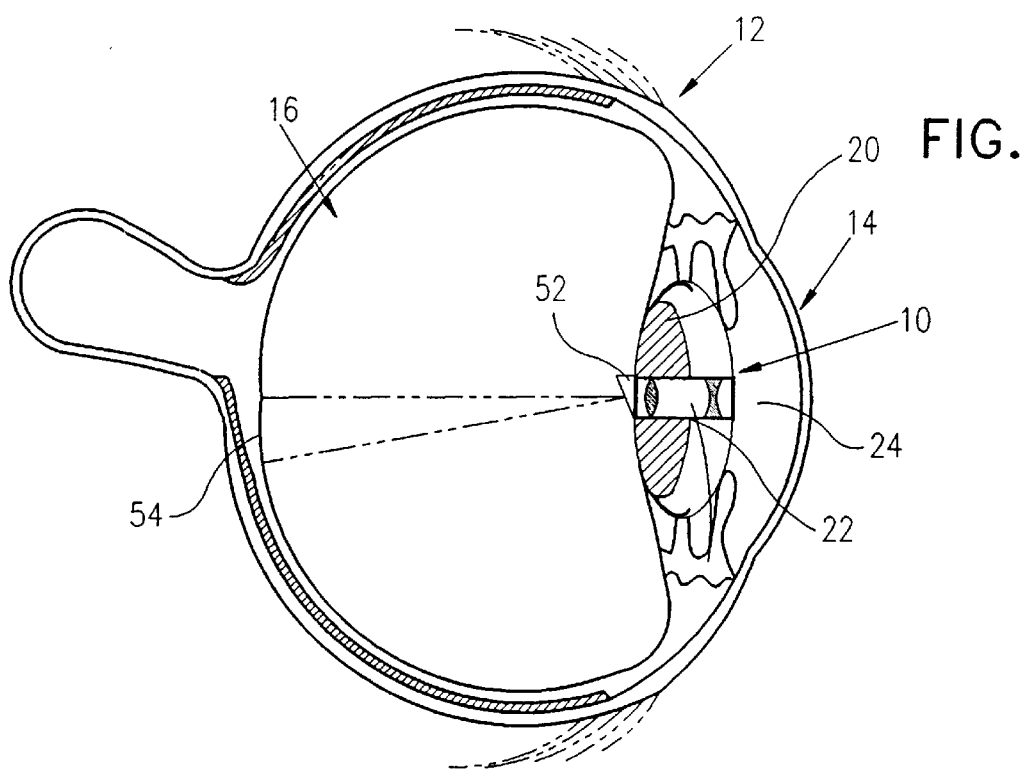
FIG. 4 is a simplified pictorial illustration of an intraocular insert, located within a human eye, of the general type shown in FIG. 1, wherein one of the windows comprises a prism.

According to another alternative embodiment of the invention, illustrated in FIG. 4, one of the windows may be in the form of a prism 52, thereby to direct light passing therethrough off-axis onto a portion 54 of the retina which lies alongside portions of the retina which may have been rendered inoperative by disease.

Figure 5:
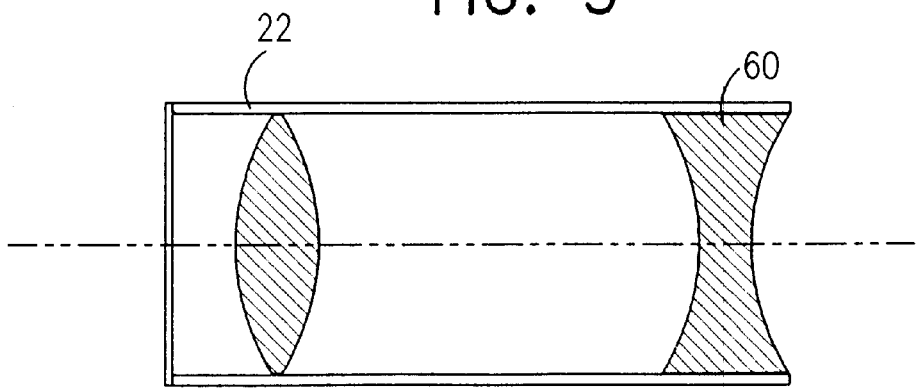
FIG. 5 is a simplified pictorial illustration of an intraocular insert of the general type shown in FIG. 1, but having only one window.

According to further alternative embodiments of the present invention, illustrated in FIG. 5, one of the windows may be eliminated and one of lenses, here indicated by reference numerals 60, also serves as a window.

Figure 6:
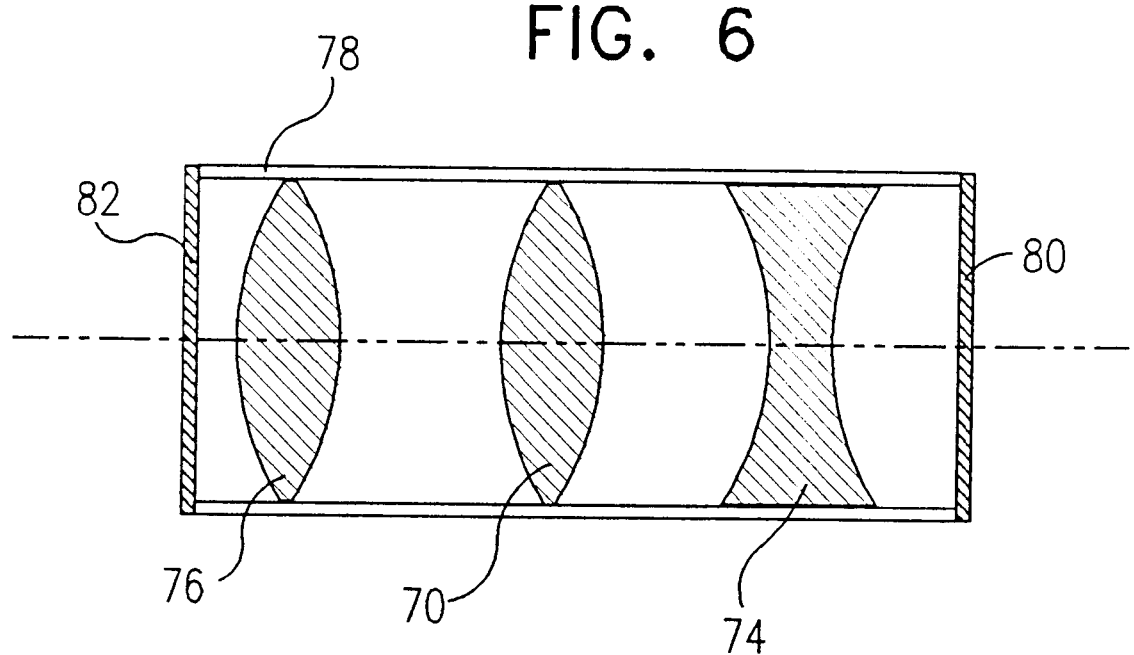
FIG. 6 is a simplified pictorial illustration of an intraocular insert of the general type shown in FIG. 1, but including more than two lenses.

According to yet another alternative embodiment of the present invention illustrated in FIG. 6, an additional lens 70 may be provided spaced from forward and rearward lenses 74 and 76 respectively along a telescope body 78 between windows 80 and 82.

Figure 7:
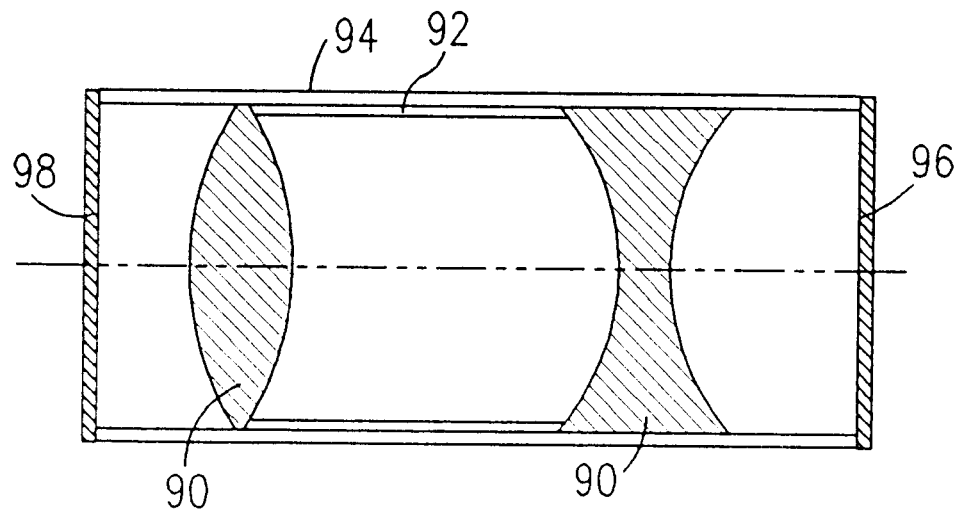
FIG. 7 is a simplified pictorial illustration of an intraocular insert of the general type shown in FIG. 1, wherein a telescope is encapsulated within an outer housing having windows.

According to yet another alternative embodiment of the present invention illustrated in FIG. 7, a plurality of lenses 90 may be joined together by a cylindrical member 92 disposed within a telescope body 94 intermediate windows 96 and 98.

It will be appreciated by persons skilled in the art that the present invention is not limited by what has been particularly shown and described hereinabove. Rather the scope of the present invention includes both combinations and subcombinations of the various features described hereinabove as well as variations and further developments thereof which would occur to persons skilled in the art upon reading the above description and which are not in the prior art.

We claim:

1. An intraocular lens implant for implantation in the interior of a human eye comprising a telescope body having an anterior end and a posterior end and including at least one window sealed to the telescope body at at least one of the anterior end and said posterior end and at least two lenses disposed within the telescope body intermediate the anterior end and the posterior end, wherein said at least two lenses are joined together by a cylindrical member disposed within the telescope body.

2. An intraocular lens implant according to claim 1 and wherein at least one of said at least two lenses are doublet lenses.

3. An intraocular lens implant according to claim 2 and wherein said at least one window is generally without optical power.

4. An intraocular lens implant according to claim 2 and wherein air gaps are defined between the lenses and between the lenses and said at least one window.

5. An intraocular lens implant according to claim 2 and wherein at least one window defines a prism.

6. An intraocular lens implant according to claim 2 and wherein said doublet lenses are joined doublet lens.

7. An intraocular lens implant according to claim 2 and wherein said doublet lenses are separated doublet lens.

8. An intraocular lens implant according to claim 1 and wherein said at least one window is generally without optical power.

9. An intraocular lens implant according to claim 8 and wherein air gaps are defined between the lenses and between the lenses and said at least one window.

10. An intraocular lens implant according to claim 8 and wherein at least one window defines a prism.

11. An intraocular lens implant according to claim 1 and wherein air gaps are defined between the lenses and between the lenses and said at least one window.

12. An intraocular lens implant according to claim 11 and wherein at least one window defines a prism.

13. An intraocular lens implant according to claim 1 and wherein at least one window defines a prism.

14. An intraocular lens implant according to claim 1 and wherein one of said lenses is a positive lens disposed towards said posterior end and another of said lenses is a negative lens disposed towards said anterior end.

* * * * *